United States Patent
Miller

(10) Patent No.: US 8,602,294 B2
(45) Date of Patent: Dec. 10, 2013

(54) SYSTEM, COMPUTER PROGRAM AND METHOD FOR MANAGING MEDICAL INFORMATION

(75) Inventor: Randy Miller, Bucyrus, KS (US)

(73) Assignee: MedicStats, LLC, Overland Park, KS (US)

(*) Notice: Subject to any disclaimer, the term of this patent is extended or adjusted under 35 U.S.C. 154(b) by 0 days.

(21) Appl. No.: 13/348,280

(22) Filed: Jan. 11, 2012

(65) Prior Publication Data

US 2013/0175334 A1 Jul. 11, 2013

(51) Int. Cl.
*G06F 17/00* (2006.01)
(52) U.S. Cl.
USPC .............. 235/375; 235/462.01; 705/2; 705/3
(58) Field of Classification Search
USPC ............................. 235/375, 462.01; 705/2, 3
See application file for complete search history.

(56) References Cited

U.S. PATENT DOCUMENTS

| | | | |
|---|---|---|---|
| 8,041,579 B2* | 10/2011 | Fotsch et al. ...................... 705/2 |
| 2003/0028493 A1* | 2/2003 | Tajima et al. ................... 705/67 |
| 2004/0205067 A1* | 10/2004 | Veidung ......................... 707/10 |
| 2005/0236483 A1* | 10/2005 | Wilz et al. ................ 235/462.01 |
| 2006/0143052 A1* | 6/2006 | Fotsch et al. ....................... 705/3 |
| 2007/0061170 A1* | 3/2007 | Lorsch ................................ 705/3 |
| 2008/0086475 A1* | 4/2008 | Kane .................................. 707/9 |
| 2009/0019552 A1* | 1/2009 | McLaughlin et al. ........... 726/27 |
| 2009/0055222 A1* | 2/2009 | Lorsch ................................ 705/3 |
| 2009/0108057 A1* | 4/2009 | Mu et al. ........................ 235/375 |
| 2009/0138281 A1* | 5/2009 | Hacker .............................. 705/3 |
| 2010/0114602 A1* | 5/2010 | Joao et al. .......................... 705/2 |
| 2010/0191772 A1* | 7/2010 | Brown et al. ................. 707/796 |
| 2010/0219241 A1* | 9/2010 | Corwin et al. ................ 235/375 |
| 2010/0287001 A1* | 11/2010 | Pearce et al. ...................... 705/2 |
| 2011/0092825 A1* | 4/2011 | Gopinathan et al. .......... 600/483 |
| 2011/0145014 A1* | 6/2011 | Avneri ............................... 705/3 |
| 2011/0246230 A1* | 10/2011 | Sie et al. ............................ 705/3 |
| 2011/0270632 A1* | 11/2011 | Manning et al. .................. 705/3 |
| 2012/0122397 A1* | 5/2012 | Brown et al. ................. 455/41.1 |
| 2012/0191474 A1* | 7/2012 | Postrel .............................. 705/3 |

* cited by examiner

*Primary Examiner* — Tuyen K Vo
(74) *Attorney, Agent, or Firm* — Hovey Williams LLP

(57) ABSTRACT

A non-transitory computer-readable storage medium has an executable computer program stored thereon for operating a computer system. The computer program includes a code segment for receiving at the computer system medical information for an individual; a code segment for storing the medical information in a web based account hosted by the computer system; a code segment for associating the web based account with a scannable code; and a code segment for providing access to some of the medical information in the web based account to a device that is used to scan an object on which the code is printed.

11 Claims, 4 Drawing Sheets

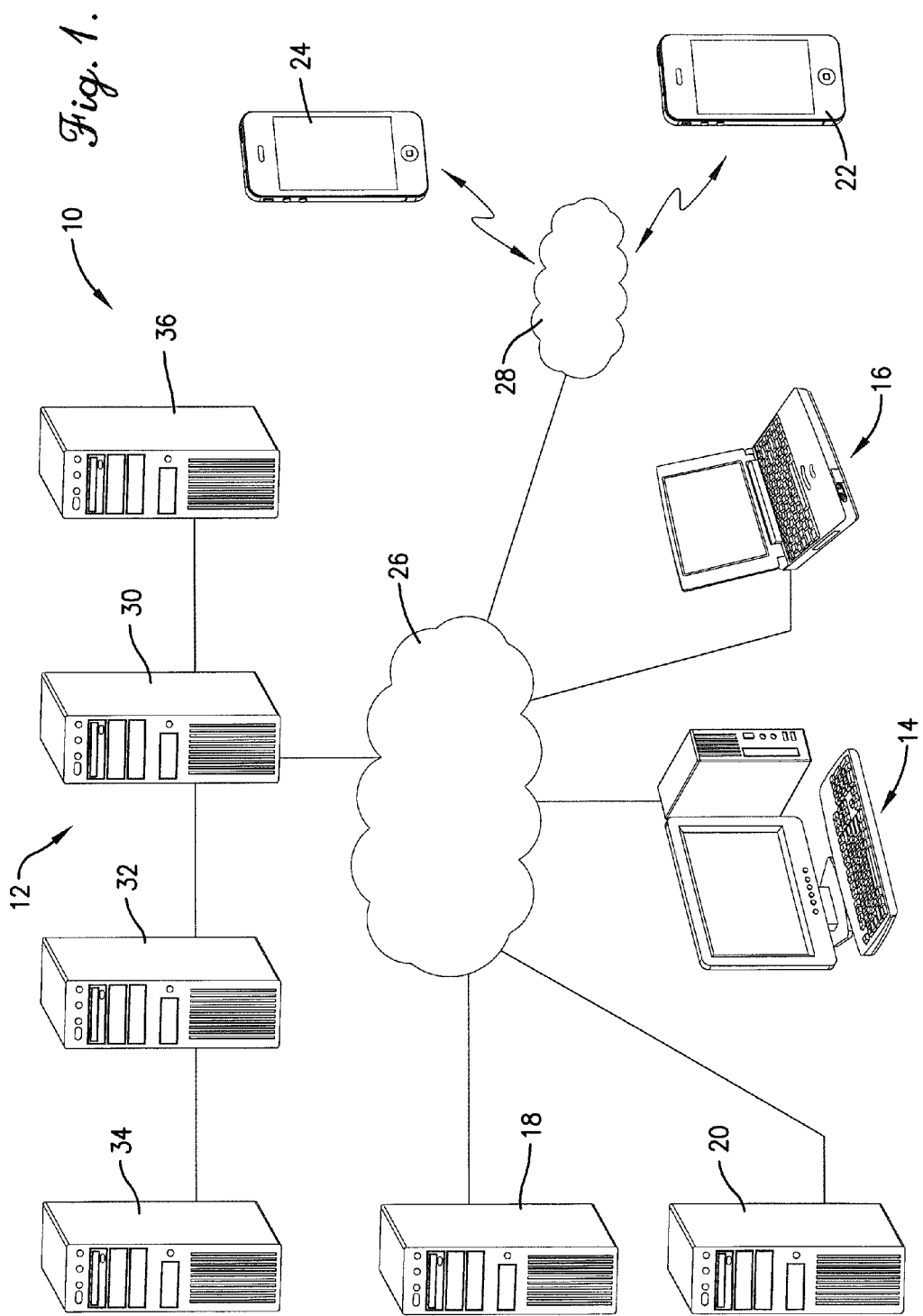

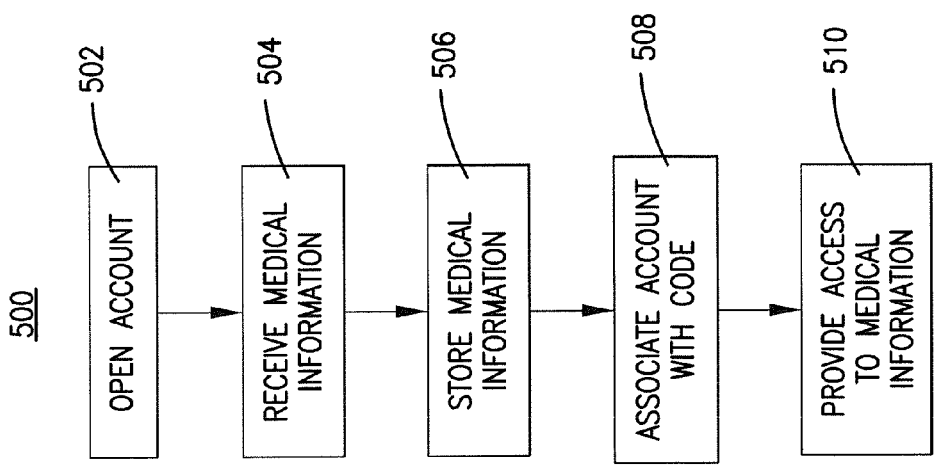

SYSTEM, COMPUTER PROGRAM AND METHOD FOR MANAGING MEDICAL INFORMATION

BACKGROUND

Patients often must provide new or updated medical information to doctors, hospitals, and other medical providers when they seek medical attention. Providing this information is time-consuming and subject to errors and omissions. Obtaining medical information from patients that have been involved in accidents or are otherwise unable to provide the information themselves is particularly difficult. In fact, ambulance operators, firefighters, and other first responders often report that the biggest problem they face is obtaining medical information from unresponsive accident victims.

To alleviate some of these problems, some people with diagnosed medical conditions and/or allergies wear bracelets or dog tags that describe their medical conditions or allergies. Unfortunately, these devices only provide the most basic medical information and are not easily updated. Many electronic medical record-keeping solutions have also been adopted and/or proposed to alleviate some of these problems, but known electronic solutions are either too complicated for practical use, limited to particular proprietary software, and/or limited in other respects.

SUMMARY

Embodiments of the present invention solve the above-described problems and related problems and provide a distinct advance in the art of medical information gathering and management.

One embodiment of the invention is a computer system that implements a web-based portal for receiving and managing medical information. An individual may access the portal and enter medical information such as a list of medical conditions, medications being taken, etc. This medical information is then stored in a personal website or other Internet accessible account designated for the individual. The account is then linked to or otherwise associated with a Quick Response (QR) code or other scannable code that includes a uniform resource locater (URL) that points to the account. The individual is then given a card, wearable tag, key chain, sticker, and/or other medium on which the QR code is printed.

The card, tag, etc. may later be scanned with a smart phone or other device with a QR reader to access the medical information in the account. For example, an ambulance operator or other first responder who is treating an accident victim may locate the victim's QR card, tag, etc., scan the QR code on the card or tag, and then nearly instantly access and view all the medical information in the victim's account. Similarly, an account holder may scan his own card or tag to access his medical information and may then instruct the computer system to e-mail or otherwise transfer some or all of the medical information to a computer system operated by a doctor, hospital, etc. The account holder, or anyone authorized by the account holder, may also scan the QR code, provide log-in information, and then update or supplement the medical information in the account.

This summary is provided to introduce a selection of concepts in a simplified form that are further described in the detailed description below. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein:

FIG. 1 is a schematic diagram of exemplary computer and communications equipment that may be used to implement embodiments of the invention.

FIG. 5 is a flow chart that depicts steps in a method or code segments of a computer program of the present invention.

Figure 3:
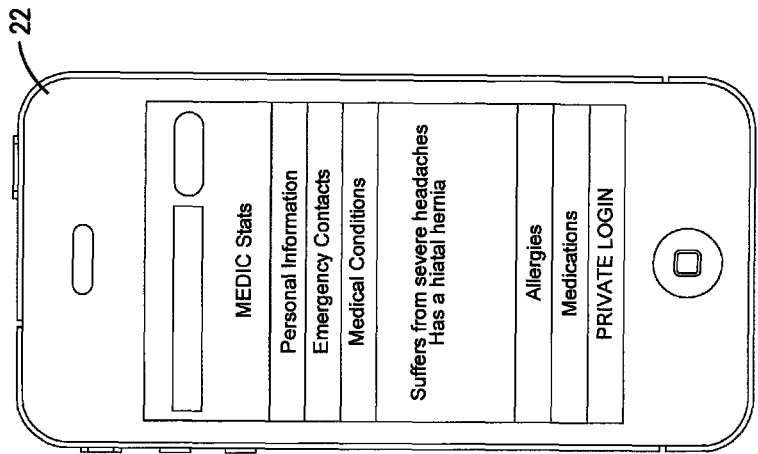
FIG. 3 is an exemplary screen display that may be presented on the mobile phone of FIG. 2 after it has been used to scan the ID card.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description of embodiments of the invention references the accompanying drawings. The embodiments are intended to describe aspects of the invention in sufficient detail to enable those skilled in the art to practice the invention. Other embodiments can be utilized and changes can be made without departing from the scope of the claims. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, function, act, etc. described in one embodiment may also be included in other embodiments, but is not necessarily included. Thus, the present technology can include a variety of combinations and/or integrations of the embodiments described herein.

Embodiments of the invention provide a system and method that may be used by individuals, emergency personnel, doctors, hospitals, and other medical professionals to store, access, and manage medical information as described in more detail below. Aspects of the invention can be implemented in hardware, software, firmware, or a combination thereof. In one embodiment, the invention may be at least partially implemented with computer and communications equipment broadly referred to by the numeral 10 in FIG. 1.

An embodiment of the computer and communications equipment 10 includes a central computer system 12 for receiving, storing and managing medical information; one or more computing devices 14, 16 operated by individuals to provide medical information to the central computer system 12; one or more computing systems 18, 20 operated by medical professionals to provide medical information to and to receive medical information from the central computer system; any number of mobile devices 22, 24 for accessing the medical information stored on the central computer system; and a communications network 26 and wireless telecommunications network 28 for providing communications between the devices 12-24. The components of the computer and communication equipment 10 illustrated and described herein are merely examples of equipment that may be used to implement embodiments of the present invention and may be replaced with other equipment without departing from the scope of the present invention.

In more detail, the central computer system 12 provides a web-based portal that serves as a repository for medical information and related information and that may be accessed by individuals, medical professionals, emergency personnel, and others as described in more detail below. Embodiments of the central computer system 12 may include one or more servers running Windows; LAMP (Linux, Apache HTTP server, MySQL, and PHP/Perl/Python); Java; AJAX; NT; Novel Netware; Unix; or any other software system and includes or has access to computer memory and other hardware and software for receiving, storing, accessing, and transmitting information as described below. The central computer system 12 also includes conventional web hosting operating software, searching algorithms, an Internet connection, and is assigned a URL and corresponding domain name such as "medicstats.com" so that websites hosted thereon can be accessed via the Internet in a conventional manner.

One particular embodiment of the central computer system 12 may comprise a web server 30, a database server 32, an application server 34, and an FTP server 36. One of the servers 30-36 may host and support software and services of proprietary mobile application providers such as Google, Apple, and Blackberry. The number and type of servers in the central computer system 12 is a matter of design choice and may depend on the number of accounts stored in the system and the number of requests and other queries received by the system 12. Thus, the invention is not limited to the specific servers and other equipment described and illustrated herein.

The computing devices 14, 16 may be any devices used by individuals to access and provide information to the central computer system 12 via the communications network 26 or any other network. For example, the computing devices 14, 16 may be laptop computers, desktop computers, tablet computers, or other personal computing devices. The devices may also be wireless phones, phone-enabled personal digital assistants, phone-enabled MP3 devices, phone-enabled handheld game players, phone-enabled tablet computers, or any other wireless communication devices. Each computing device 14, 16 includes or can access an Internet browser and a conventional Internet connection such as a wired or wireless broadband connection, a modem, DSL converter, or ISDN converter so that it can access the central computer system 12 via the communications network 26 or another network.

Likewise, the computing devices 18, 20 may be any devices used by doctors, hospitals, and other medical professionals to access, provide information to, and/or receive information from the central computer system 12 via the communications network 26 or any other network. For example, the computing devices 18, 20 may be laptop computers, desktop computers, tablet computers, or other computers. The devices 18, 20 may also include wireless phones or any other wireless communication devices. Each computing device 18, 20 includes or can access an Internet browser and a conventional Internet connection such as a wired or wireless broadband connection, a modem, DSL converter, or ISDN converter so that it can access the central computer system 12 via the communications network 22 or another network.

The mobile devices 22, 24 may be wireless phones, phone-enabled personal digital assistants, phone-enabled MP3 devices, phone-enabled handheld game players, phone-enabled tablet computers, or any other portable and wireless communication devices. Each computing mobile device includes or can access an Internet browser so that it can access the central computer system 12 via the communications network 28 or another network.

The communications network 26 is preferably the Internet but may be any other communications network such as a local area network, a wide area network, or an intranet. The wireless network 28 may be any network capable of supporting wireless communications such as the wireless networks operated by AT&T, Verizon, or Sprint. The wireless network may include conventional switching and routing equipment. The communications network 26 and wireless network 28 may be combined or implemented with several different networks.

The present invention may also comprise one or more computer programs stored in or on computer-readable medium residing on or accessible by the central computer system 12 or other computer equipment. The computer programs may comprise listings of executable instructions for implementing logical functions in the computer equipment. The computer programs can be embodied in any computer-readable medium for use by or in connection with an instruction execution system, apparatus, or device, such as a computer-based system, processor-containing system, or other system that can fetch the instructions from the instruction execution system, apparatus, or device, and execute the instructions. In the context of this application, a "computer-readable medium" can be any non-transitory means that can contain, store, or communicate the programs. The computer-readable medium can be, for example, but not limited to, an electronic, magnetic, optical, electro-magnetic, infrared, or semi-conductor system, apparatus, or device. More specific, although not inclusive, examples of the computer-readable medium would include the following: an electrical connection having one or more wires, a portable computer diskette, a random access memory (RAM), a read-only memory (ROM), an erasable, programmable, read-only memory (EPROM or Flash memory), an optical fiber, and a portable compact disk read-only memory (CDROM).

The above-described computer and communications equipment 10 may be used to implement a web-based portal for receiving and managing medical information. As described in more detail below, an individual may access the portal and enter medical information such as a list of medical conditions, medications being taken, etc. This medical information is then stored in a personal website or other Internet accessible account. The account is then associated with a Quick Response (QR) code or other scannable code that includes a uniform resource locater (URL) that points to the account. The individual is then given a card, wearable tag, key chain, sticker, and/or other medium on which the QR code is printed. The card, tag, etc. may later be scanned with a smart phone or other device with a QR reader to access the medical information in the account.

The flow chart of FIG. 5 shows the functionality and operation of a preferred implementation of the present invention in more detail. In this regard, some of the blocks of the flow chart may represent method steps and/or a module segment or portion of code of the computer programs of the present invention. In some alternative implementations, the functions noted in the various blocks may occur out of the order depicted in FIG. 5. For example, two blocks shown in succession in FIG. 5 may in fact be executed substantially concurrently, or the blocks may sometimes be executed in the reverse order depending upon the functionality involved.

An individual (also occasionally referred to herein as an "account holder") is first prompted to open an account with the entity that provides the services of the present invention as depicted in block 502. This may be done on-line, in-person, or over the phone and may require the individual to provide contact and identification information and pay for the services in a conventional manner.

The account holder is then prompted to provide medical information to the central computer system as depicted in block 504. The medical information may include personal information such as the individual's sex, date of birth, race, etc.; a list of medical conditions; a list of allergies; a list of medications being taken; and/or any other information that may be useful in providing medical care to the individual. The medical information may be provided in a variety of manners. In one embodiment, the computer system 12 presents an on-line template that may be accessed with one of the computers 14, 16 and populated with requested medical information. In other embodiments, the medical information may be provided by medical professionals using one of the computers 18, 20. In still other embodiments, the medical information may be provided in hand-written documents and transcribed into the central computer system 12.

Each account holder may also designate whether his or her medical information is public or private. For example, an individual may designate the list of allergies and medications as public but designate certain personal information as private. The purpose of this distinction is described below.

The central computer system 12 then stores at least some of the medical information in a personal mobile website or other Internet accessible account created for the account holder as depicted in block 406. The mobile website is assigned its own unique uniform resource locator (URL) and may be stored in the computer system along with websites for other account holders.

Each website or other Internet-accessible account is then associated with a Quick Response (QR) code, a Micro QR code, or any other type of scannable code as depicted in block 408. The scannable code stores the URL for the website and possibly other information. Thus, the central computer system may store Internet-accessible medical information accounts for a number of account holders, but each account has its own unique URL and is associated with its own unique QR code or other scannable code.

The QR code or other scannable code for an account holder is then printed on one or more ID cards, wearable tags, key chains, stickers, or other objects that are then given to the account holder. The individual is then instructed to carry and/or wear the objects on which the codes are printed.

Figure 2:
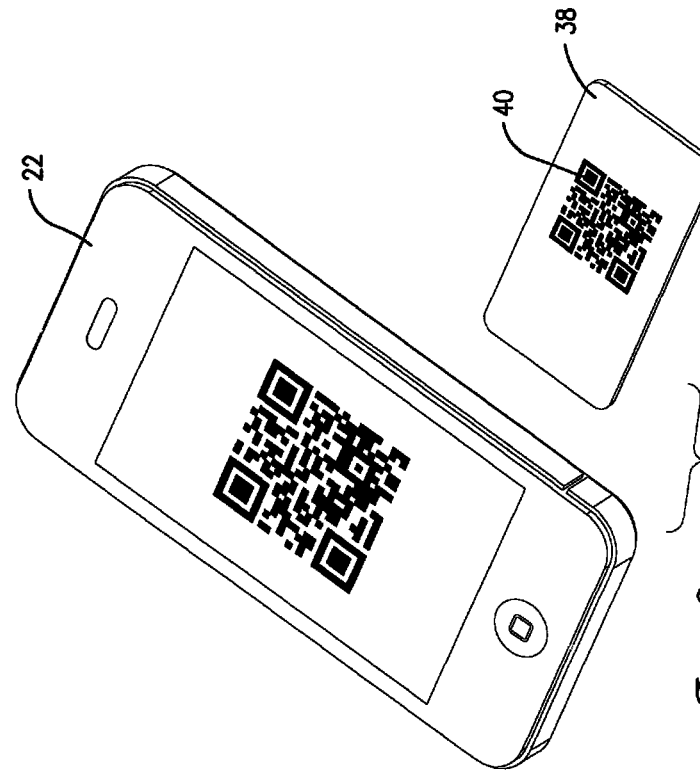
FIG. 2 shows a mobile phone being used to scan an ID card on which a QR code has been printed.

The individual, an emergency responder, a doctor, or anyone else may then scan the code with a mobile phone or any other device with a QR reader as depicted in FIG. 2. A web browser on the mobile phone then opens the website associated with the code so that the person operating the mobile phone can view the medical information stored in the medical account as depicted in block 410. For example, an ambulance operator or other first responder who is treating an accident victim may locate the victim's QR card, tag, etc., scan the QR code on the card or tag, and then nearly instantly access and view all the medical information in the victim's account.

Similarly, the account holder may scan his own card or tag to access his medical information and may then instruct the computer system to e-mail or otherwise transfer some or all of the medical information to a computer system operated by a doctor, hospital, etc. The account holder, or anyone authorized by the account holder, may also scan the QR code, provide log-in information, and then update or supplement the medical information in the account.

When an object on which a QR code is scanned as depicted in FIG. 2, the mobile phone or other device may be presented with the screen shown in FIG. 3. This screen allows the person operating the mobile phone to access any of the stored medical information for the individual by pressing a virtual button or other input on a touch screen display. For example, if the user of the mobile phone presses the "Medical Conditions" button, the mobile phone may open up and display the messages "Suffers from Severe Headaches" and "Has a Hiatal Hernia" as depicted in FIG. 3.

Figure 4:
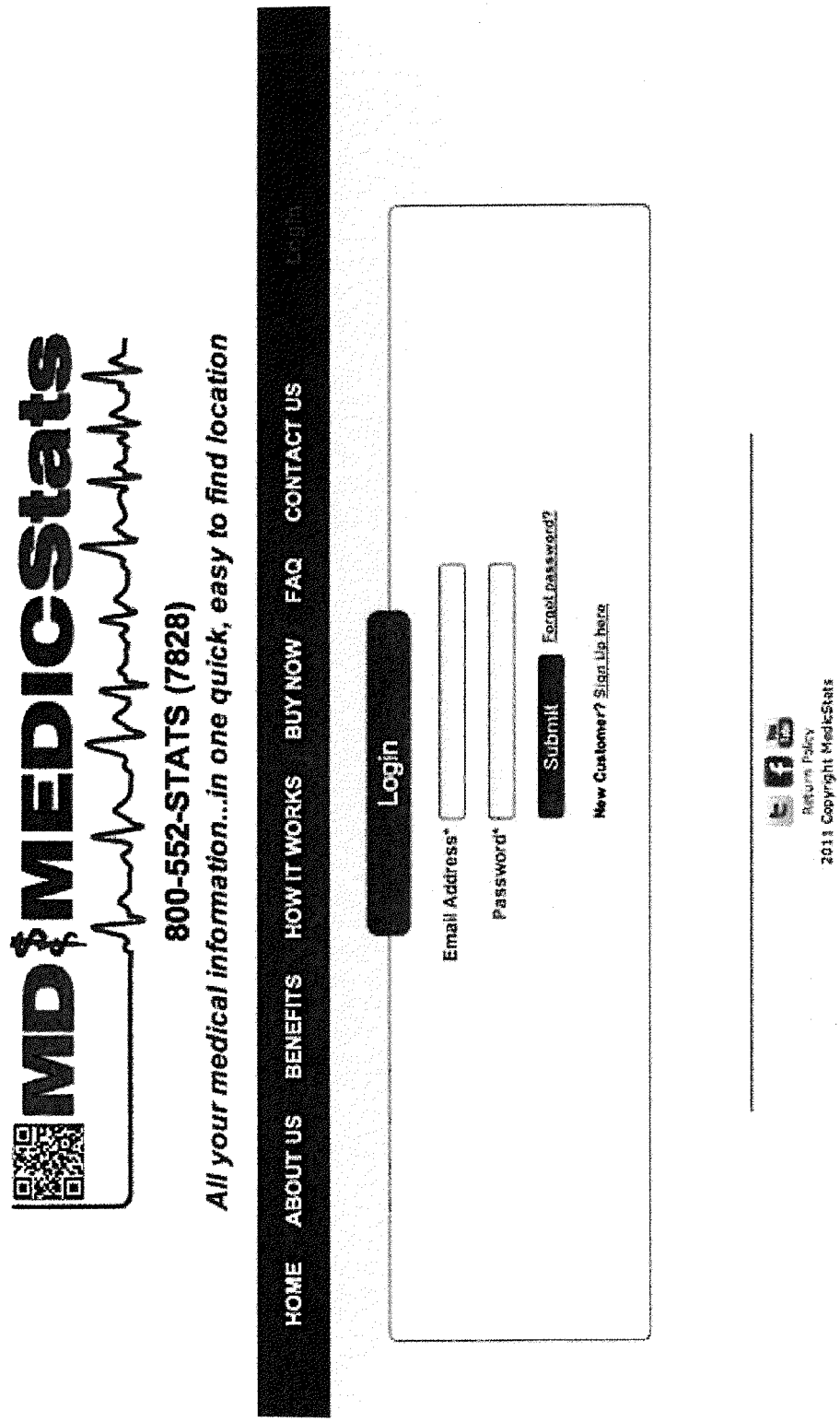
FIG. 4 is another exemplary screen display that may be presented on the mobile phone of FIG. 2 after an account holder or other authorized person elects to log-in to an account.

An account holder, or anyone else authorized by the account holder, may also update or supplement his or her medical information by selecting a "Private Login" button shown in FIG. 3 and then entering an authorized e-mail address and password as shown in FIG. 4. The Private Login may also provide access to the account holder's private medical information, whereas the public medical information may be accessed by anyone who simply scans the QR code.

In other embodiments, an account may be associated with two QR codes: one that provides access to the account holder's public information and another that provides access to the private information or both the public information and the private information. This allows an account holder to give an ID card or other object on which the public QR code is printed to some people and to give an ID card on which the private QR code is printed to other people. For example, the pubic QR code may be printed on a sticker that is applied to the account holder's automobile and/or front door and the private QR code may be printed on ID cards that the account holder may give to only selected people.

The central computer system 12 may also permit an account holder to e-mail or otherwise transfers some or all of the person's medical information to a doctor or other person. This functionality may be provided by a screen display or button that can be reached after a private log-in.

The central computer system 12 may also allow account holders to link their accounts with accounts for other people. For example, an individual may link his or her account to an account of a relative or friend who is frequently with the individual. This allows an emergency responder to quickly and easily obtain medical information for multiple people who may be travelling together by scanning a single QR code on an object carried by or worn by one of the people.

Account holders may also link their accounts to emergency contacts that are automatically called, texted, or e-mailed whenever the account is accessed. For example, an account holder that is a minor may list her parent's cell phone number and/or e-mail address in an "automatic contact" list. Then whenever the minor's account is accessed, the parent may receive a text or e-mail. This allows the parent to control, or at least monitor, access to the minor's medical information and alerts the parent in the event the minor is receiving medical attention.

Although the invention has been described with reference to the preferred embodiment illustrated in the attached drawing figures, it is noted that equivalents may be employed and substitutions made herein without departing from the scope of the invention as recited in the claims.

Having thus described the preferred embodiment of the invention, what is claimed as new and desired to be protected by Letters Patent includes the following:

1. A non-transitory computer-readable storage medium with an executable computer program stored thereon for operating a computer system, the computer program comprising:
   a code segment for providing a template that may be accessed via the Internet and populated with medical information for an individual;
   a code segment for storing the medical information in a personal web based account hosted by the computer system, wherein the personal web based account is associated with a unique uniform resource locator (URL);
   a code segment for partitioning the web based account into a public section storing a first portion of the medical information and a private section storing a second portion of the medical information;
   a code segment for associating the public section of the web based account with a first scannable code that stores the unique URL for the web based account;
   a code segment for permitting the individual or a person authorized by the individual to log-in to the web based account and update, change or supplement the medical information in the web based account;
   a code segment for providing access to the first portion of the medical information in the web based account stored in the public section to a mobile phone or other mobile device that is used to scan an object on which the first scannable code is printed;
   a code segment for receiving an access request from the mobile phone or other mobile device when the first scannable code is scanned, and directing the mobile phone or other mobile device directly to the public section of the personal web based account associated with the unique URL; and
   a code segment for directing the mobile phone or other mobile device from the public section of the personal web based account to the private section upon inputting authorized login information.

2. The computer-readable storage medium as set forth in claim 1, further comprising:
   a code segment for permitting the individual or a medical professional to access the computer system and update and/or supplement the medical information in the web based account.

3. The computer-readable storage medium as set forth in claim 1, further comprising:
   a code segment for associating the web based account with a second scannable code, wherein the second scannable code is associated with the private section; and
   a code segment for receiving an access request from the mobile phone or other mobile device when the second scannable code is scanned, and directing the mobile phone or other mobile device directly to the private section of the personal web based account.

4. The computer-readable storage medium as set forth in claim 1, wherein the object on which the scannable code is printed is an information card, a wearable tag, a key chain, or a sticker.

5. The computer-readable storage medium as set forth in claim 1, wherein the medical information includes personal information about the individual, emergency contact information for the individual, medical conditions of the individual, suffered by the individual, and medications taken by the individual.

6. A computer-implemented method of managing medical information, the method comprising the steps of:
   providing a template that may be accessed via the Internet and populated with medical information for an individual, wherein the medical information includes emergency contact information of at least one emergency contact individual;
   storing the medical information in a personal web based account hosted by the computer system;
   associating the web based account with a first scannable code that stores a uniform resource locator (URL) for the web based account;
   providing access to some of the medical information in the web based account to a mobile device that is used to scan an object on which the first scannable code is printed;
   permitting the individual or a person authorized by the individual to log-in to the web based account and update, change or supplement the medical information in the web based account;
   attempting to notify the at least one emergency contact individual when the first scannable code is scanned and the account is accessed; and
   associating the web based account with a second scannable code, wherein the web based account is partitioned into a public section and a private section, and the first scannable codes is associated with the public section and the second scannable code is associated with the private section.

7. The method as set forth in claim 6, further comprising the steps of linking at least a second account of another individual to the web based account; and providing access to some of the medical information in the second account to the mobile phone or other mobile device, wherein the emergency contact information includes at least one telecommunication number associated with the at least one emergency contact individual, wherein the step of attempting to notify the at least one emergency contact individual includes the step of automatically dialing the telecommunication number.

8. The method as set forth in claim 6, wherein the medical information further includes a contact list which comprises the emergency contact information.

9. The method as set forth in claim 6, wherein the emergency contact information includes at least one telecommunication number associated with the at least one emergency contact individual, and the step of attempting to notify the at least one emergency contact individual includes the step of automatically dialing the telecommunication number.

10. The method as set forth in claim 6, wherein the emergency contact information includes at least one telecommunication number associated with the at least one emergency contact individual, and the step of attempting to notify the at least one emergency contact individual includes the step of attempting to transmit a text-based message over a telecommunication network.

11. The method as set forth in claim 6, further comprising the steps of linking at least a second account of another individual to the web based account, and providing access to some of the medical information in the second account to the mobile phone or other mobile device.

* * * * *